(12) United States Patent
Bennett

(10) Patent No.: US 7,096,721 B2
(45) Date of Patent: Aug. 29, 2006

(54) CORROSION COUPON RACK AND COUPON HOLDER

(76) Inventor: Richard J. Bennett, 408 Riverside Dr., Washington, NC (US) 27889

( * ) Notice: Subject to any disclaimer, the term of this patent is extended or adjusted under 35 U.S.C. 154(b) by 45 days.

(21) Appl. No.: 10/983,401

(22) Filed: Nov. 8, 2004

(65) Prior Publication Data

US 2006/0096360 A1    May 11, 2006

(51) Int. Cl.
- *G01N 17/04* (2006.01)
- *G01D 21/00* (2006.01)
- *F16L 55/07* (2006.01)
- *F16L 35/00* (2006.01)

(52) U.S. Cl. .................. 73/86; 73/866.5; 324/71.2; 324/700; 285/93

(58) Field of Classification Search ............ 73/86, 73/866.5; 324/71.2, 700; 285/93
See application file for complete search history.

(56) References Cited

U.S. PATENT DOCUMENTS

| | | | |
|---|---|---|---|
| 1,769,463 A * | 7/1930 | Rice ................ | 73/86 |
| 3,976,313 A | 8/1976 | Lauffenburger et al. | |
| 4,120,313 A | 10/1978 | Lewis | |
| 4,179,920 A | 12/1979 | Schuller et al. | |
| 4,222,593 A | 9/1980 | Lauffenburger | |
| 4,697,465 A | 10/1987 | Evans et al. | |
| 5,049,492 A | 9/1991 | Sauer et al. | |
| 5,150,065 A | 9/1992 | Luna | |
| 5,338,069 A | 8/1994 | McCarthy | |
| 5,854,557 A | 12/1998 | Tiefnig | |
| 5,927,760 A | 7/1999 | Rocha | |
| 6,077,418 A | 6/2000 | Iseri et al. | |
| 6,131,443 A | 10/2000 | Duncan | |
| 6,206,431 B1 | 3/2001 | Street | |
| 6,412,827 B1 | 7/2002 | Barclay et al. | |
| 6,508,274 B1 | 1/2003 | Street | |
| 6,628,111 B1 | 9/2003 | Shapiro et al. | |

* cited by examiner

*Primary Examiner*—Daniel S. Larkin
(74) *Attorney, Agent, or Firm*—MacCord Mason PLLC

(57) ABSTRACT

A corrosion coupon rack includes one or more coupon mounting devices constructed of a coupon holder receiver including a handle recess of a given diameter and an end wall, a connection conduit in communication with the handle recess through an opening in the end wall and axially aligned therewith, and locking means having open and closed positions, the locking means including a cam surface extending into the handle recess when the locking means is in the closed position; and a coupon holder including a handle insertable into the handle recess, the handle having inner and outer ends, a locking recess, and a shaft axially aligned with the handle, the shaft having a proximal end attached to the handle inner end, and a distal end adapted to releasibly attach a corrosion coupon, the shaft extending through the T-connection and into the pipe.

20 Claims, 3 Drawing Sheets

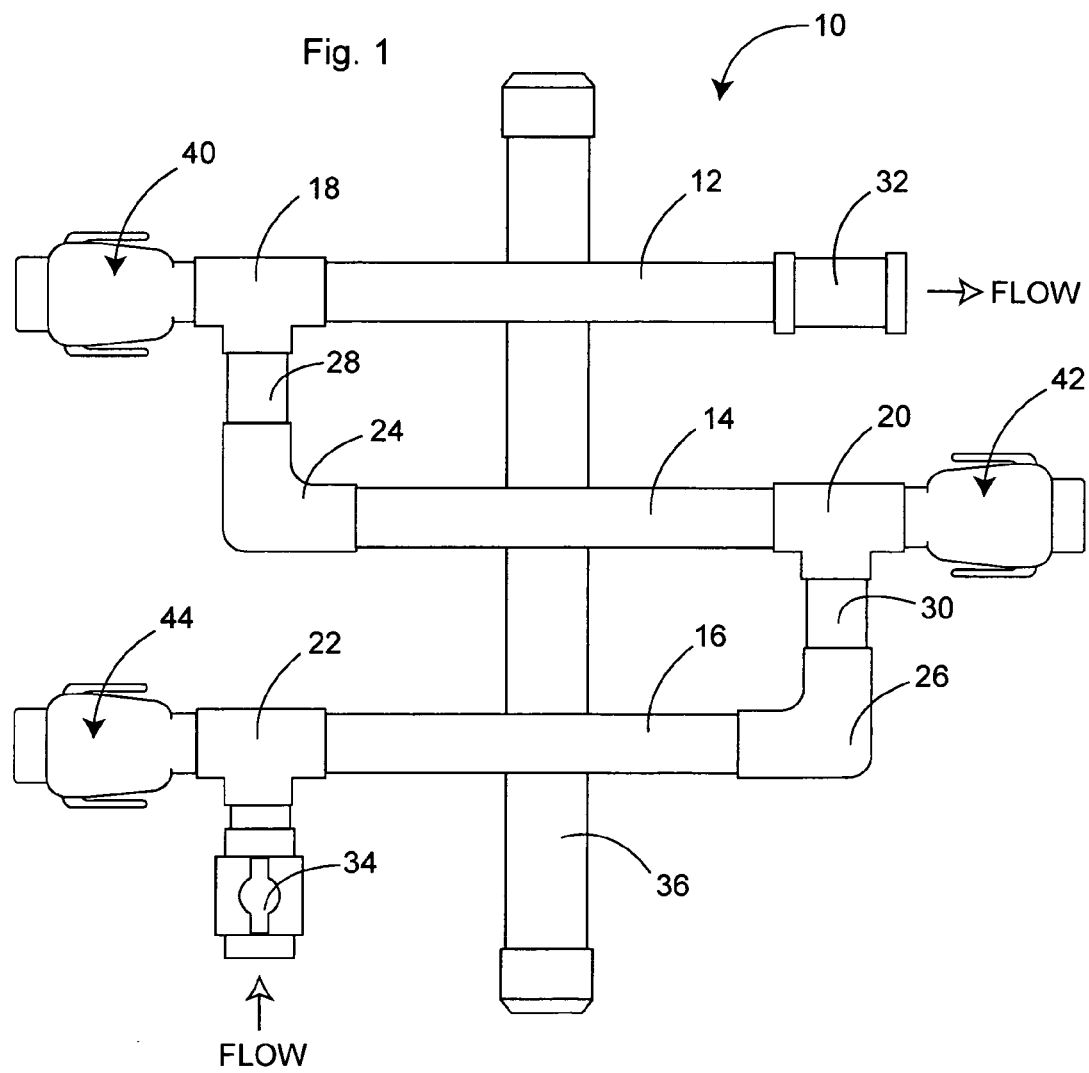

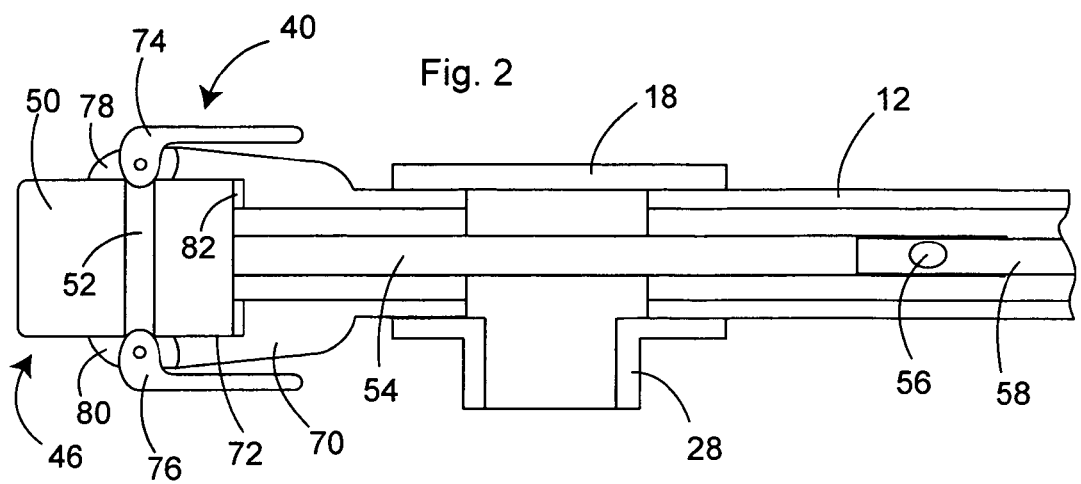
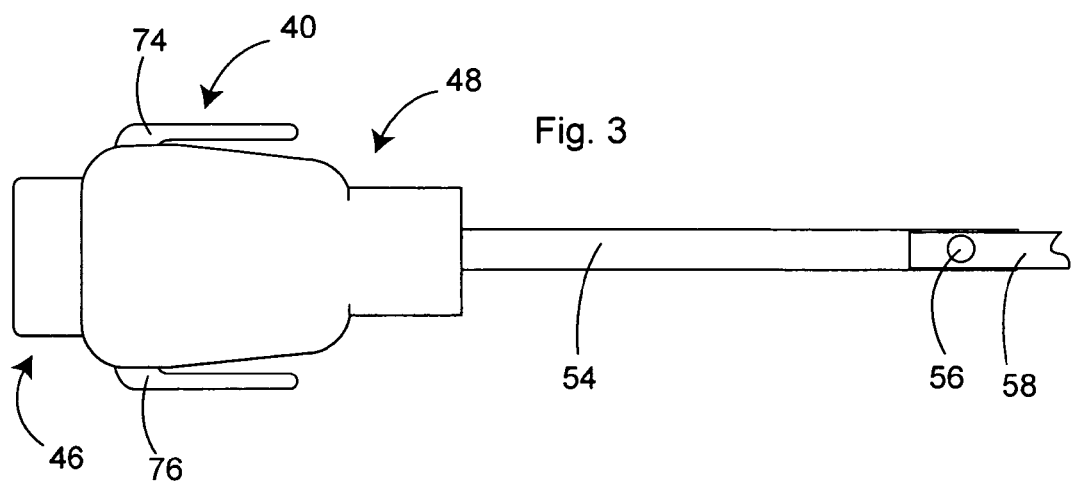
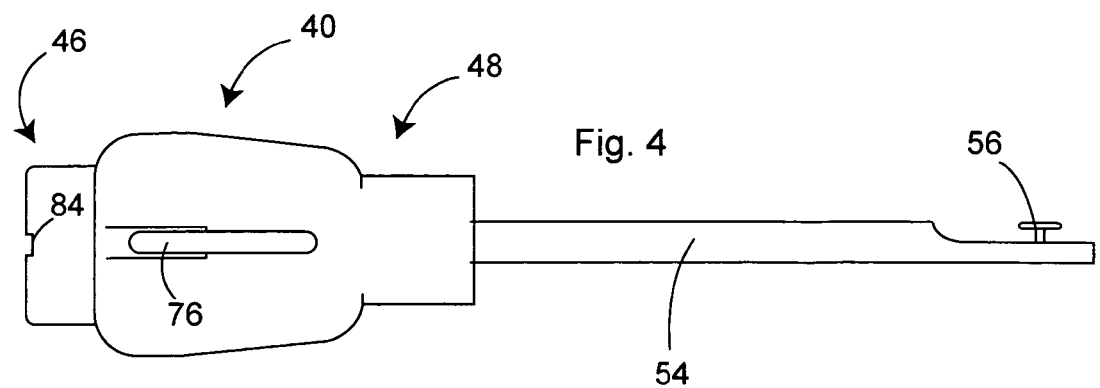

CORROSION COUPON RACK AND COUPON HOLDER

BACKGROUND OF THE INVENTION (1) Field of the Invention

The present invention relates to a corrosion coupon rack of the type used to support coupons within a liquid conduit to evaluate corrosion, and in particular to a rack including coupon holders that can be rapidly and easily removed and reinserted into the rack.

(2) Description of the Prior Art

Corrosion coupon racks provide a convenient means of monitoring the progress of corrosion in systems such as boilers, condensate lines, open recirculating cooling water, closed circulating hot or chilled water systems, etc. By monitoring the corrosion rate of inexpensive coupons, information is obtained that can avoid damage to expensive piping systems. A corrosion rack creates a side stream off the main system in which corrosion test coupons can be exposed to system water under controlled and reproducible conditions.

Corrosion racks used in conjunction with high temperature and high pressure installations are constructed of black iron pipe, while corrosion racks used in low temperature systems are normally constructed of PVC pipe, e.g., one inch pipe with corresponding T-joints, elbows, valves, etc. The rack is normally arrayed in a zig-zag fashion and may include one or more, e.g., up to six, coupon holders that are normally positioned at the outer ends of T-connectors so that the coupon held by the coupon holder extends into a horizontal pipe on the opposite side of the T-connector. Water is then conveyed though the vertical section of the T-connector and though the horizontal pipe, flowing over the coupon. Generally, the coupons, which are conventionally thin bars of metal, e.g., mild carbon steel or copper, are removed from the pipe for examination anywhere from monthly to yearly, e.g., every 90 days, depending on the corrosion conditions. The corrosion coupons are visually examined, weighed, and evaluated for corrosion rate, and pitting severity.

Conventional coupon holders are comprised of a shaft with a distal end adapted to detachably support a coupon, and a proximal end attachable to a threaded cap that is screwed onto the rack to position the shaft and an attached coupon into a horizontal pipe. Many caps require a tool for removal, although some coupon racks purport to use caps that can be unscrewed by hand without the use of a tool. In any event, the necessity of unscrewing coupon holders to remove or replace coupons is laborious and time consuming, particularly if a large number of coupon holders are involved. Therefore, there is a need for an improved corrosion coupon holder, and a corrosion coupon rack that includes one or more of such holders, that can be quickly and easily removed and replaced, while securely holding the coupon in place without leakage when in position.

SUMMARY OF THE INVENTION

Generally, the coupon rack of the present invention is comprised of a plurality of horizontal pipe sections, each having an upstream end connected to one horizontal arm of a first T-connector. The downstream end of the horizontal pipe is connected via an elbow connector and a short length of vertical pipe to the vertical leg of a second T-connector, or to a downstream valve. The rack also includes an upstream valve connected to piping joining the vertical leg of a first T-connector. The pipes, T-connectors, elbows and valves are connected to each other to provide for fluid flow communication through the rack components, with the water entering the upstream valve and then sequentially through each of the T-connectors and pipes until exiting through the downstream valve.

A coupon mounting device is attached to a horizontal arm of each T-connector on the opposite side of the T-connector from a horizontal pipe. The coupon mounting device of the present invention is comprised of a coupon holder to releasibly support the coupon in one of the rack pipes, and a coupon holder receiver attachable to one of the T-connectors for releasibly mounting the holder. Generally, the coupon holder is comprised of a handle, preferably a cylindrical handle, and a coupon shaft axially aligned with the handle. The handle includes inner and outer ends, and a locking recess, preferable in the form of a circumferential groove around the handle between its ends. The shaft is connected at its proximal end to the inner end of the handle, with the distal end of the shaft being adapted for releasible attachment of a coupon. For example, the distal end of the shaft may include a cutout area with a non-corrosive pin to attach a coupon with an attachment hole to the distal end of the shaft.

The coupon holder receiver, or receiver, is comprised of a housing having a handle recess with a continuous side wall and an end wall corresponding to the shape of the holder handle. A conduit having a smaller diameter sized for insertion into the horizontal arm of a T-connector connects to the recess through an opening in the end wall. The receiver further includes a locking means that is insertable into the locking recess in the holder handle. Preferably, the locking means is in the form of opposed pivotal levers having cams on their inner ends, with the levers being pivotal between open and locking positions. When the levers are in the locking position, the cams extend through slots into the receiver housing to engage the handle groove. The housing further includes a resilient arcuate seal or washer at the joinder of the cylindrical bore and the conduit against the recess end wall around the conduit opening. Movement of the levers to their locked positions urges the handle inwardly, compressing the seal and providing a water-tight connection.

BRIEF DESCRIPTION OF THE DRAWINGS

FIG. 1 is a perspective view of a coupon rack with three coupon holders.

FIG. 2 is a sectional side view of the coupon mounting device of the present invention within a rack.

FIG. 3 is a side view of the coupon mounting device of the present invention.

FIG. 4 is a top view of the coupon mounting device of the present invention.

DETAILED DESCRIPTION OF THE INVENTION

Figure 5:
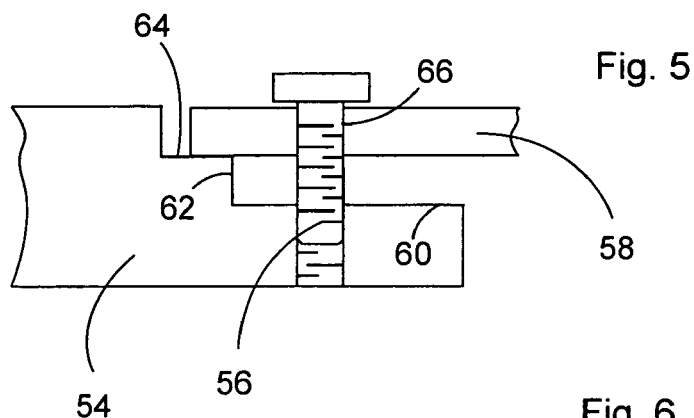
FIG. 5 is a detailed sectional side view of the connection of a coupon to the coupon holder with the coupon in the insertion position.

In the following description, terms such as horizontal, upright, vertical, above, below, beneath, and the like, are used solely for the purpose of clarity in illustrating the invention, and should not be taken as words of limitation. The drawings are for the purpose of illustrating the invention and are not intended to be to scale.

As best shown in FIG. 1, coupon rack, generally 10, is comprised of pipes 12, 14 and 16 that are connected at their upstream ends to T-connectors 18, 20 and 22, respectively. The downstream ends of pipes 14 and 16 are connected through elbows 24 and 26 and short pipe sections 28 and 30 to the vertical legs of T-connectors 18 and 20, respectively. The downstream end of pipe 12 is connected to a cutoff valve 32 used to prevent backflow of water into the system. The vertical leg of T-connector 22 is connected via pipe section to ball valve 34 used to prevent the flow of water into the rack. Rack 10 is shown mounted on unistrut 36.

Coupon mounting devices 40, 42 and 44 are inserted into the horizontal arms of T-connectors 18, 20 and 22 opposite pipes 12, 14 and 16, respectively. As illustrated in detail in FIGS. 2–4, each coupon mounting device is comprised of a coupon holder, generally 46, and a coupon holder receiver, generally 48. The numbering of FIGS. 2–4 is with reference specifically to coupon mounting device 40 and corresponding rack components. However, since all coupon mounting devices are of the same construction, it will be understood that FIGS. 2–4 and the description thereof apply equally to all coupon mounting devices.

FIG. 2 is a sectional side view of coupon mounting device 40 attached to T-connector 18, which in turn is attached to pipe 12 and pipe section 28. FIG. 3 is a side view of coupon mounting device 40. FIG. 4 is a top view of coupon mounting device 40.

Coupon holder 46 is comprised of cylindrical handle 50, which includes circumferential groove 52, and shaft 54 axially aligned with handle 50 and projecting from the inner side of handle 50 through T-connector 18 and into, and axially aligned with, pipe 12. Attachment pin 56 secures coupon 58 to the distal end of shaft 54 through a hole in coupon 58.

Figure 6:
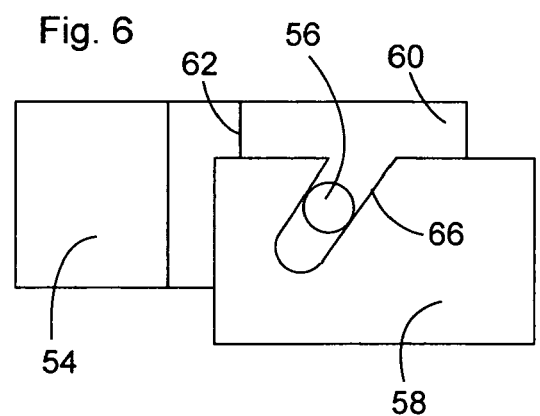
FIG. 6 is a detailed top view of the connection of a coupon to the coupon holder with the coupon in the insertion position, and the bolt top removed for clarity.
Figure 7:
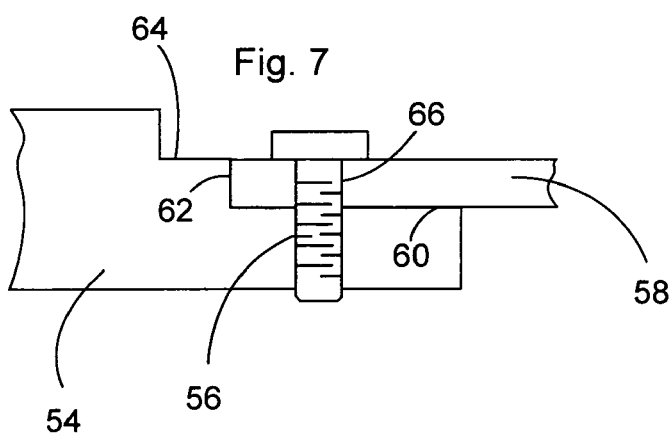
FIG. 7 is a detailed sectional side view of the connection of a coupon to the coupon holder with the coupon in the locked position.
Figure 8:
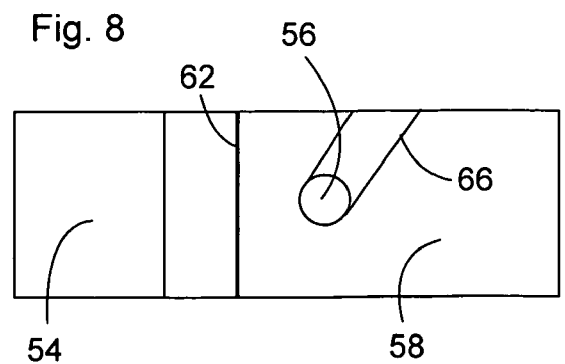
FIG. 8 is a detailed top view of the connection of a coupon to the coupon holder with the coupon in the locked position, and the bolt top removed for clarity.

As shown in detail in FIGS. 5–8, the distal end of shaft 54 includes a coupon-receiving ledge 60 with a rear transverse shoulder 62, and may include an upper ledge 64. Coupon 58 includes an angled slot 66. In order to attach coupon 58, pin 56 is loosened and slot 66 is inserted around pin 56 with coupon 58 riding along upper ledge 64. When pin 56 is fully inserted into slot 66, coupon 58 drops to ledge 60 and pin 56 is tightened locking coupon 58 in place, with rotation of coupon 58 being prevented by shoulder 62.

Coupon holder receiver 48 is comprised of housing 70 which includes a cylindrical recess 72 with a continuous side wall and an end wall to slidably receive handle 50 and opposed pivotal levers 74 and 76, which are pivotal between open and locked positions within slots 78 and 80, respectively, in housing 70. Levers 74 and 76 include cam surfaces on their inner ends that are inserted into groove 52 when levers 74 and 76 are moved to their locked position. Annular resilient seal 82 is positioned between the end wall of recess 72 and the inner end of handle 50. When positioning holder 46 in receiver 48, it is desirable to orient coupon 58 vertically within pipe 12 for optimal corrosion test results. Therefore, handle 50 includes a position indicator in the form of radial slot 84 on the outer end of handle 50. Rotation of handle 50 until slot 84 is vertically aligned results in vertical alignment of coupon 58.

In operation, valves 32 and 34 are closed, and levers 74 and 76 are raised to their open position separating their cam surfaces from groove 52, freeing coupon holder 46 for slidable movement. Holder 46 is then withdrawn from receiver 48 by pulling on handle 50. A coupon 58 is then attached to the distal end of shaft 54, and holder 46 is then reinserted into receiver 48. Levers 74 and 76 are then returned to their locked positions forcing their cam surfaces into groove 52 to lock holder 46 within receiver 48. Pivoting of levers 74 and 76 to the locked position also urges handle 50 inwardly compressing seal 82 to create a watertight closure.

Certain modifications and improvements will occur to those skilled in the art upon a reading of the foregoing description. For example, it will be apparent that a greater or lesser number of coupon mounting devices can be used, and that the handle can be other than cylindrical. It should be understood that all such modifications and improvements have been deleted herein for the sake of conciseness and readability but are properly within the scope of the following claims.

What is claimed is:

1. A coupon mounting device for use in a coupon rack comprising:
   a) a coupon holder including a handle with a given diameter, inner and outer ends, and a locking recess, and a shall axially aligned with said handle, said shall having a proximal end attached to said handle inner end, and a distal end adapted for releasable attachment to a corrosion coupon; and
   b) a coupon holder receiver having a handle recess with an inner diameter corresponding to said handle given diameter and an end wall, and a connection conduit in communication with said handle recess through said end wall and axially aligned therewith, and locking means having open and locked positions, said locking means including a cam surface extending into said handle recess when said locking means is in the locked position.

2. The coupon mounting device of claim 1, wherein said coupon holder handle is cylindrical.

3. The coupon mounting device of claim 1, wherein said shaft includes a coupon attachment pin and is adapted for attachment to a corrosion coupon having a pin-receiving hole.

4. The coupon mounting device of claim 1, wherein said locking recess is a groove around said handle.

5. The coupon mounting device of claim 1, further including an annular resilient seal against said handle recess end wall.

6. The coupon mounting device of claim 1, wherein said locking means is comprised of at least one pivotal lever having a cam surface insertable into said locking recess when said locking means is in its locked position.

7. The coupon mounting device of claim 1, wherein said shaft distal end includes a coupon-receiving ledge with a rear transverse shoulder and a pin having a raised position and a locking position projecting upwardly from said ledge, said coupon having a slot insertable over said pin, whereby said coupon is locked against said ledge and said shoulder when said pin is in said locking position.

8. A coupon mounting device for use in a coupon rack comprising:
   a) a coupon holder including a cylindrical handle with a given diameter, inner and outer ends, and a circumferential groove between said inner and outer ends, and a shaft axially aligned with said handle, said shaft having a proximal end attached to said handle inner end, and a distal end adapted for releasable attachment of a corrosion coupon; and b) a coupon holder receiver including i) a cylindrical handle recess with an inner diameter corresponding to said handle given diameter and an inner end wall, ii) a connection conduit in communication with said handle recess through an opening in said end wall and axially aligned with said recess, said conduit having an inner diameter smaller than the inner diameter of said handle recess, and iii) pivotal levers having open and locked positions, said levers including cam surfaces extending into said handle recess when said levers are in the locked position to engage said circumferential groove.

9. The coupon mounting device of claim 8, wherein said shaft includes a coupon attachment pin and is adapted for attachment to a corrosion coupon having a pin-receiving hole.

10. The coupon mounting device of claim 8, further including an annular resilient seal mounted against said handle recess end wall.

11. The coupon mounting device of claim 8, wherein said handle includes a position indicator on its outer end and is rotatable within said handle recess.

12. A corrosion coupon rack comprising:
a) a first T-connector having inner and outer horizontal arms and a vertical leg in communication with said arms;
b) a horizontal pipe having an upstream end in fluid flow communication with said first T-connector inner arm, and a downstream end;
c) a coupon holder receiver extending from said T-connector outer arm, said receiver including a handle recess of a given diameter and an end wall, and a connection conduit in communication with said handle recess through an opening in said end wall and axially aligned therewith, and locking means having open and closed positions, said locking means including a cam surface extending into said handle recess when said locking means is in the closed position; and d) a coupon holder including a handle insertable into said handle recess, said handle having inner and outer ends, and a latching recess, and a shaft axially aligned with said handle, said shaft having a proximal end attached to said handle inner end, and a distal end adapted to releasibly attach a corrosion coupon, said shaft extending through said T-connector and into said pipe.

13. The corrosion coupon rack of claim 12, wherein said coupon holder handle is cylindrical.

14. The corrosion coupon rack of claim 12, wherein said shaft includes a coupon attachment pin and is adapted for attachment to a corrosion coupon having a pin-receiving hole.

15. The corrosion coupon rack of claim 12, wherein said latching recess is a groove around said handle.

16. The corrosion coupon rack of claim 12, further including an annular resilient seal mounted against said handle recess end wall.

17. The corrosion coupon rack of claim 12, wherein said locking means is comprised of at least one pivotal lever having a cam surface insertable into said locking recess when said locking means is in its locked position.

18. The coupon mounting device of claim 12, wherein said shaft distal end includes a coupon-receiving ledge with a rear transverse shoulder and a pin having a raised position and a locking position projecting upwardly from said ledge, said coupon having a slot insertable over said pin, whereby said coupon is locked against said ledge and said shoulder when said pin is in said locking position.

19. The corrosion coupon rack of claim 12, wherein the vertical leg of said first T-connector is in fluid flow communication with a second T-connector having an attached coupon holder receiver and coupon holder.

20. The corrosion coupon rack of claim 12, wherein said pipe downstream end is in fluid flow communication with a third T-connector having an attached coupon holder receiver and coupon holder.

* * * * *